US011649257B2

(12) United States Patent
Pucheault et al.

(10) Patent No.: US 11,649,257 B2
(45) Date of Patent: May 16, 2023

(54) COMPOSITION OF 7,9-DODECADIENYL-1-ACETATE ISOMERS AND PROCESS FOR PRODUCTION THEREOF

(71) Applicants: Universite de Bordeaux, Bordeaux (FR); Institut Polytechnique de Bordeaux, Talence (FR); Centre National de la Recherche Scientifique (CNRS), Paris (FR)

(72) Inventors: Mathieu Pucheault, Camblanes et Meynac (FR); Virginie Liautard, Begles (FR); Loic Guillonneau, Pau (FR); Olivier Guerret, Pern (FR)

(73) Assignees: Universite de Bordeaux; Institut Polytechnique de Bordeaux; Centre National de la Recherche Scientifique (CNRS)

( * ) Notice: Subject to any disclaimer, the term of this patent is extended or adjusted under 35 U.S.C. 154(b) by 287 days.

(21) Appl. No.: 16/492,256

(22) PCT Filed: Mar. 9, 2018

(86) PCT No.: PCT/EP2018/055956
§ 371 (c)(1),
(2) Date: Sep. 9, 2019

(87) PCT Pub. No.: WO2018/162739
PCT Pub. Date: Sep. 13, 2018

(65) Prior Publication Data
US 2020/0354387 A1    Nov. 12, 2020

(30) Foreign Application Priority Data

Mar. 10, 2017 (FR) ...................................... 1751979

(51) Int. Cl.
*C07F 9/141* (2006.01)
*C07C 69/587* (2006.01)

(52) U.S. Cl.
CPC .......... *C07F 9/141* (2013.01); *C07B 2200/09* (2013.01); *C07C 69/587* (2013.01)

(58) Field of Classification Search
USPC ......................................................... 563/23
See application file for complete search history.

(56) References Cited

U.S. PATENT DOCUMENTS

| | | |
|---|---|---|
| 3,394,201 A | 7/1968 | Adams et al. |
| 3,845,108 A | 10/1974 | Kochansky et al. |
| 3,954,818 A | 5/1976 | Labovitz et al. |
| 4,014,946 A | 3/1977 | Labovitz et al. |
| 4,912,253 A | 3/1990 | Fukumoto et al. |
| 2010/0113837 A1 | 5/2010 | Bedoukian et al. |
| 2017/0137447 A1 | 5/2017 | Dufour et al. |

FOREIGN PATENT DOCUMENTS

| | | |
|---|---|---|
| EP | 0241335 A1 | 10/1987 |
| FR | 2341546 A1 | 9/1977 |
| WO | 2016001383 A1 | 1/2016 |

OTHER PUBLICATIONS

March'S Advanced Organic Chemistry (5th Ed. 2001), 151-155.*
Real World Drug Discovery, Rydzewski (2008), 42-43.*
Chong JM, Heuft MA. Hydroalumination of 3-butyn-1-ol: Application to a stereoselective synthesis of (3E, 5Z)-3, 5-dodecadienyl acetate, the sex pheromone of the leaf roller moth. Tetrahedron. Dec. 10, 1999;55(50):14243-50.
Negishi EI, Yoshida T, Abramovitch A, Lew G, Williams RM. Highly stereoselective syntheses of conjugated E, E- and E, Z-dienes, E-enynes and E-1, 2, 3-butatriened via alkenylborane derivatives. Tetrahedron. Jan. 1, 1991;47(3):343-56.
Negishi EI, Abramovitch A. A highly efficient chemo- , regio- , and stereoselective synthesis of (7E, 9Z)-dodecadien-1-yl acetate, a sex pheromone of Lobesia botrana, via a functionalized organoborate. Tetrahedron Letters. Jan. 1, 1977;18(5):411-4.
Unelius CR, Liblikas I, Mozuraitis R. Synthesis and characterization of the four geometrical isomers of 3, 5-dodecadienyl acetate. Acta Chemica Scandinavica. 1998;52(7):930-4.
Kudo E, Sasaki K, Kawamata S, Yamamoto K, Murahashi T. Selective E to Z isomerization of 1, 3-Dienes Enabled by A Dinuclear Mechanism. Nature communications. Mar. 5, 2021;12(1):1-8.
Negishi EI, Hu Q, Huang Z, Qian M, Wang G, Brown H. Palladium-catalyzed alkenylation by the Negishi coupling. Aldrichim. Acta. Jan. 1, 2005;38:71-87.
Ragoussis V, Panopoulou M, Ragoussis N. Concise preparation of the (3 E, 5 Z)-alkadienyl system. New approach to the synthesis of principal insect sex pheromone constituents. Journal of agricultural and food chemistry. Aug. 11, 2004;52(16):5047-51.
Yadav JS, Reddy EJ. Synthesis of (3 E, 5 Z)-3, 5-Dodecadienylacetate, the Sex Pheromone of Phtheochroa cranaodes (Lepidoptera: Tortricidae). Bioscience, biotechnology, and biochemistry. Jan. 1, 2000;64(8):1726-8.
Alexakis, et al., "A New Approach to Conjugated Dienes Synthesis of the Pheromones of LOBESJA BOTRANA and BOMBYX MORJ," Tetrahedron, Jan. 1, 1989, pp. 381-389, No. 45, No. 2.

(Continued)

*Primary Examiner* — Ana Z Muresan
(74) *Attorney, Agent, or Firm* — Lerner David LLP

(57) ABSTRACT

The present invention relates to a process for preparing a mixture M1 of enol phosphate isomers devoid of (E,E) isomer and comprising at least 98% of (E,Z) isomer, at least 0.1% of (Z,Z) isomer and at least 0.1% of (Z,E) isomer, comprising bringing a mixture of isomers of said enol phosphate comprising a detectable amount of (E,E) isomer into contact with a hydrolysable dienophile in an organic solvent, followed by base hydrolysis of the medium obtained and elimination of the adduct formed, in order to obtain the mixture M1 devoid of (E,E) isomer.

7 Claims, No Drawings

(56) References Cited

OTHER PUBLICATIONS

Cassani, et al., "Synthesis of LOBESIA BOTRANA and SPODOPTERA LITTORALIS Natural Sex-Attractants," Tetrahedron Letters, 1980. pp. 3497-3498, vol. 21.
Ideses, et al., "Sex Pheromone of the European Grapevine Moth, *Lobesia botrana* Schiff. (Lepidrpters: Tortricidae) Synthesis and Effect of Isomeric Purity on Biological Activity," Journal of Chemical Ecology, (Received Mar. 12, 1981; Revised May 12, 1981), pp. 195-200, vol. 8, No. 1.
International Search Report for Application No. PCT/EP2018/055956 dated Apr. 4, 2018, 2 pages.
Preliminary Search Report for Application No. FR1751979 dated Oct. 13, 2017, 2 pages.
Cahiez, G. et al., "Efficient Preparation of Terminal Conjugated Dienes by Coupling of Dienol Phosphates with Grignard Reagents under Iron Catalysis," Organic Letters, May 2008, pp. 2389-2392, vol. 10(12).
Wender, P.A. et al., "Transition Metal-Catalyzed Intramolecular [4+2] Cycloadditions: Mechanistic and Synthetic Investigations," Tetrahedron, Feb. 1998, pp. 1255-1275, vol. 54(7).

\* cited by examiner

COMPOSITION OF 7,9-DODECADIENYL-1-ACETATE ISOMERS AND PROCESS FOR PRODUCTION THEREOF

CROSS-REFERENCE TO RELATED APPLICATIONS

The present application is a national phase entry under 35 U.S.C § 371 of International Application No. PCT/EP2018/055956 filed Mar. 9, 2018, which claims priority from French Application No. 1751979 filed Mar. 10, 2017, all of which are hereby incorporated herein by reference.

OBJECT OF THE INVENTION

The present invention concerns a mixture of 7,9-dodecadienyl-1-acetate isomers, whose 7E, 9Z is the sex hormone for the European grapevine moth, *Lobesia botrana*, a lepidopteran grapevine pest. This composition is characterized in that its isomeric purity is greater than or equal to 98% in (7E,9Z) isomer and that it contains at 0.1% of at least one of the (7Z,9E) and (7Z,9Z) isomers, and less than 1% of (7E,9E) isomer. This composition extremely rich in grapevine moth pheromone is obtained from a new two-step process with a yield of at least 55%.

For reasons of public health and management of soil agricultural potential, technologies for treating crops against pests are evolving toward more targeted and environmentally-friendly modes of action. To this end, the use of sex pheromones to change the behavior of insects has advantages since these pheromones are specific to each species of pest and are effective at very low doses, in various strategies (trapping and sexual confusion, for example).

However, development of these technologies is hindered by the cost of access to active molecules. Indeed, these molecules often have many possible isomers and selective synthesis technologies are generally costly.

Furthermore, the principle of using pheromones to combat insects such as the grapevine moth consists, in particular of embedding the signal emitted by the females of the species in a cloud of pheromone diffused in the grapevines by means, for example, of a large number of diffusers (see, for example, BASF's RAK system or Shin-Etsu Chemical's Isonet system). What guarantees the efficacy of these diffusers is the dose of active isomer per hectare. However, today these diffusers are filled with isomer mixes only containing 75% by weight of the active isomer. This leads to unnecessary expense and requires spreading a unnecessary quantity of chemical product in the fields. From this viewpoint, it is therefore important to be able to prepare isomer mixtures that are as concentrated as possible in the right isomer.

Finally, it may be problematic to use mixtures containing too many isomers which are not normally present in *Lobesia* pheromone. Indeed, these other isomers may be pheromones for other insects, which destroys the argument of selectivity of pheromone-based products.

The primary component of grapevine moth sex pheromone is (E,Z)-7,9-dodecadienyl-1-acetate. This molecule bears two double bonds and therefore has four possible geometric isomers as seen in the following table:

TABLE 1

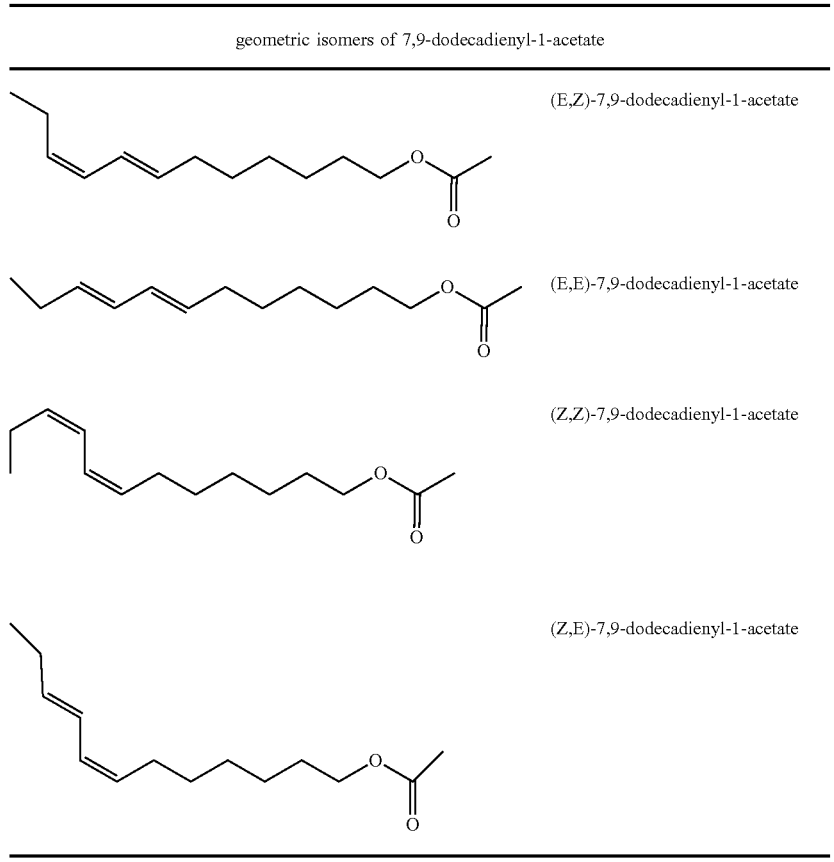

geometric isomers of 7,9-dodecadienyl-1-acetate

To effectively respond to the economic problem posed by the synthesis of this pheromone, the following items should be considered:

Only the (E,Z) isomer is active. It is therefore essential to be able to prepare it predominantly. Among all these isomers, the thermodynamically most stable isomer is the (E,E) isomer.

It is important to note that the three isomers other than (E,Z) are known as not hindering the attractiveness of the pheromone (Ideses et al. *Journal of Chemical Ecology*, Vol. 8, No. 1, 1982, p. 195).

The (E,E) isomer is the most stable isomer and is the main inactive impurity in all known syntheses.

Likewise, a certain number of other pheromones of agricultural pests comprise a conjugated diene unit, and the process of the present invention may therefore be applied to them. The following molecules can be named, in particular: (E,Z)-2,4-Decadienal, (Z,E)-3,5-Decadienyl acetate, Ethyl (E,Z)-2,4-decadienoate, Methyl (E,Z)-2,4-decadienoate, (E,Z)-3,5-Dodecadienyl acetate, (E,Z)-4,6,10-Trimethyl-2,4-dodecadien-7-one, (E,Z)-5,7-Dodecadien-1-ol, (E,Z)-5,7-Dodecadienal, (E,Z)-5,7-Dodecadienyl acetate, (E,Z)-7,9-Dodecadien-1-ol, (E,Z)-7,9-Dodecadienal, (E,Z)-7,9-Dodecadienyl acetate, (E,Z)-8,10-Dodecadien-1-ol, (E,Z)-8,10-Dodecadienal, (E,Z)-8,10-Dodecadienyl acetate, (Z,E)-3,5-Dodecadienyl acetate, (Z,E)-3,7,11-Trimethyl-2,4,10-dodecatriene, (Z,E)-3,7,11-Trimethyldodeca-2,4-diene, (Z,E)-5,7-Dodecadien-1-ol, (Z,E)-5,7-Dodecadienal, (Z,E)-5,7-Dodecadienyl acetate, (Z,E)-5,7-Dodecadienyl propionate, (Z,E)-7,9-Dodecadien-1-ol, (Z,E)-7,9-Dodecadienyl acetate, (Z,E)-8,10-Dodecadien-1-ol, (Z,E)-8,10-Dodecadienal, (Z,E)-8,10-Dodecadienyl acetate, (Z,Z)-5,7-Dodecadienal, (Z,Z)-5,7-Dodecadienyl acetate, (Z,Z)-7,9-Dodecadien-1-ol, (Z,Z)-7,9-Dodecadienyl acetate, (Z,Z)-8,10-Dodecadien-1-ol, (Z,Z)-8,10-Dodecadienyl acetate, (E,Z)-10,12-Tetradecadienyl acetate, (E,Z)-3,5-Tetradecadienoic acid, (E,Z)-3,5-Tetradecadienyl acetate, (E,Z)-8,10-Tetradecadienal, (E,Z)-8,10-Tetradecadienyl acetate, (E,Z)-9,11-Tetradecadienyl acetate, (Z,E)-10,12-Tetradecadienyl acetate, (Z,E)-3,5-Tetradecadienyl acetate, (Z,E)-8,10-Tetradecadien-1-ol, (Z,E)-8,10-Tetradecadienyl acetate, (Z,E)-9,11-Tetradecadien-1-ol, (Z,E)-9,11-Tetradecadienal, (Z,E)-9,11-Tetradecadienyl acetate, (Z,Z)-10,12-Tetradecadien-1-ol, (Z,Z)-10,12-Tetradecadienyl acetate, (Z,Z)-3,5-Tetradecadienoic acid, (Z,Z)-8,10-Tetradecadienal, (Z,Z)-9,11-Tetradecadien-1-ol, (Z,Z)-9,11-Tetradecadienal, (Z,Z)-9,11-Tetradecadienyl acetate, (E,Z)-8,10-Pentadecadien-1-ol, (E,Z)-8,10-Pentadecadienyl acetate, (E,Z)-9,11-Pentadecadienal, (Z,E)-8,10-Pentadecadienyl acetate, (Z,Z)-8,10-Pentadecadienyl acetate, (Z,Z)-9,11-Pentadecadienal, (E,Z)-10,12-Hexadecadien-1-ol, (E,Z)-10,12-Hexadecadienal, (E,Z)-10,12-Hexadecadienyl acetate, (E,Z)-11,13-Hexadecadien-1-ol, (E,Z)-11,13-Hexadecadienal, (E,Z)-11,13-Hexadecadienyl acetate, (E,Z)-9,11-Hexadecadienal, (E,Z)-9,11-Hexadecadienyl acetate, (Z,E)-10,12-Hexadecadienal, (Z,E)-10,12-Hexadecadienyl acetate, (Z,Z)-8,10-Heptadecadien-1-ol.

Patent application WO2016001383 describes a new, two-step synthesis pathway for diene compounds of the general formula

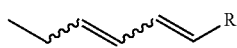

using an intermediate compound like dialkyl or diaryl-hexa-1,3-dien-1-yl phosphate of general formula 2

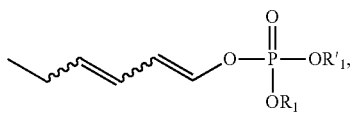

wherein $R_1$ and $R'_1$ independently designate an alkyl group or an aryl group.

Therefore, in the case of (E,Z)-7,9-dodecadienyl-1-acetate synthesis, this two-step synthesis permits obtaining a final isomer mixture predominantly composed of the (E,Z) isomer, typically between 70% and 80%, a second predominant (E,E) isomer, typically in a proportion of 20% to 30%, and the two other isomers in proportions below 1%.

One object of the present invention is a synthesis process that allows simply producing an isomer mixture M1 of compound 2 free of the (E,E) isomer in a first step. Then, in a second step, a composition M2 of 7,9-dodecadienyl-1-acetate isomers with a very high content of (E,Z) isomer and very low contents of the other isomers can be obtained. Typically, M2 has an isomeric purity greater than or equal to 98% in (E,Z) isomer and contains at least 0.1% of (Z,E) and (Z,Z) isomers and less than 1% of (E,E) isomer.

STATE OF THE ART

From the viewpoint of isomeric purity, examining the solutions proposed in the prior art to obtain 7,9-dodecadienyl-1-acetate reveals two main classes of proposed solutions:

A first class groups synthesis pathways that mainly focus on achieving high stereoselectivity (greater than 95%). Generally, the (E,Z)-7,9 dodecadienyl-1-acetate pheromone is obtained after a large number of steps, including one that leads to a final, nearly pure (E,Z) intermediate to attain the highest possible isomeric purity and for which the secondary isomer is (E,E) isomer. In these types of syntheses, the secondary (Z,Z) and (Z,E) isomers are absent.

In U.S. Pat. No. 3,954,818 the authors describe a synthesis in more than 9 steps with an unspecified yield and an E,Z)-7,9-dodecadienyl-1-acetate pheromone purity close to 99%. However, since the key intermediate of this process is 7-E-dodecen-9-ynol, the authors naturally obtained a mixture of (E,Z) and (E,E) isomers for the pheromone. Furthermore, it is necessary to note that this process is difficult to envisage industrially due to the reagents used (lithium wire, butyl lithium, disiamylborane, etc.) and is not advantageous from the economic viewpoint due to the number of steps.

In U.S. Pat. No. 3,845,108A, the process consists of 8 synthesis steps for an overall yield of 30% from the fourth step and a final purity of only 70%. The process is characterized by an iminophosphonate intermediate and the use of industrially unusable reagents (mercury oxide). Chromatographic analysis of the final compound gives the proportion of 9:1 for (E,Z) and (E,E) isomers of 7,9-dodecadienyl-1-acetate.

In FR 2341546A1, a 9-step synthesis is found, the second-to-last step leading to obtaining isomerically-pure (E,Z) 7,9-dodecadienol after recrystallization at −40° C. After the final step, (E,Z)-7,9-dodecadienyl-1-acetate is obtained with a proportion of 92% and isomer (E,E)-7,9-dodecadienyl-1-acetate with a content of 8% (vapor phase chromatographic analysis).

In a second class of synthesis methods, isomeric purity is not the purpose and the percentage of isomeric purity is generally fairly low.

In EP 0241335, the authors describe a process in 5 synthesis steps with an overall yield of approximately 10%. The isomeric purity of the pheromone is at least 75% because the stereochemistry of the double bond in position 9 results from a Wittig reaction involving propyl-triphenylphosphonium ylide and leads to a cis/trans ratio of 75/25 of this double bond. The other isomer from this synthesis is therefore (E,E). This expensive process requires equipment for hydrogenation under pressure.

Furthermore, the Wittig reaction generates large quantities of triphenyl phosphine oxide that are expensive to eliminate.

U.S. Pat. No. 4,912,253 claims the synthesis of European grapevine moth pheromone by a copper-catalyzed coupling between a magnesium compound (chloropentanol derivative) and (E,Z)-2,4-heptadienyl acetate. The acetate derivative preparation is difficult, however, and this access pathway, while convergent, remains expensive. The (E,Z)-7,9-dodecadienyl-1-acetate isomer is obtained with a purity of 92% with no further specifications about the proportion of other isomers. However, the authors explain that a partial isomerization of the Z bond occurred during the catalytic coupling reaction in the presence of a mixed copper/lithium catalyst, therefore leading to the presence of the (E,E) isomer.

In U.S. Pat. No. 7,932,410, a general process for forming dienes conjugated to a long fat chain is described, and is characterized by the use of esters with a double bond in the alpha position, such as 1-penten-3-yl isobutyrate which is coupled to a Grignard reagent via a catalyst based on copper complexes. This process is not applicable industrially to the synthesis of (E,Z)-7,9 dodecadienyl-1-acetate since the 1,3-hept-dien-3-yl isobutyrate necessary for this synthesis is very difficult to access industrially. Moreover, the isomeric purities are not given for (E,Z)-7,9 dodecadienyl-1-acetate, whose synthesis by this process is not described. The other syntheses lead to very average isomeric purities.

In Alexakis et al. Tetrahedron, vol. 45, no. 2, p. 389, 1989, the authors describe an eight-step process that exploits the reactivity of epoxide functions in the presence of silicon derivatives. The stereoisomeric selectivity is very high, around 96.5% in (E,Z)-7,9 dodecadienyl-1-acetate isomer. The authors show that the double bond in position 7 can only be trans, which implies that only a mix of (E,Z) and (E,E) isomers can be obtained by this synthesis pathway.

Finally, purification methods are commonly used to enrich the mixtures obtained in (E,Z) isomer, in particular by reducing the proportion of (E,E) isomer. Thus, purification with urea is often cited, but does not lead to very substantial (E,Z) purities.

Another technique for eliminating (E,E) isomer is suggested but not described in Cassani et al., Tet. Let. 80, 1980, p. 3497; it consists of reacting the isomer mixture in tetracyanoethylene then doing a separation on a chromatographic column. The need for this column separation makes this process unsuitable to industrialization.

Finally, the shortest synthesis pathway is the one described in WO2016001383 and the applicant discovered a means for rendering selective the synthesis methods for 7,9-dodecadienyl acetate, in particular the process described in WO2016001383, to the point of leading to an original mixture M2 of 7,9-dodecadienyl acetate isomers characterized in that its isomeric purity is greater than or equal to 98% in (E,Z) isomer and that M2 contains at least 0.1% of (Z,E) and (Z,Z) isomers and less than 1% of (E,E) isomer.

The new process of the present invention consists of reacting an enol phosphate of formula 1 with a hydrolyzable dienophile and of observing, surprisingly, that only (E,E) isomer reacts to give an adduct which, after basic hydrolysis, becomes soluble in water and can be very easily removed. This purification of the key intermediate allows then reacting this intermediate while conserving the isomer ratio.

Hydrolysable dienophile means, according to the applicant, a dienophile (concept known to the skilled person) such as the product of the Diels-Alder reaction that can be easily transformed into a salt soluble in water, for example at pH≥8.

In the sense of the present invention and as well known to the skilled person, a dienophile is a molecule, in the sense of the Diels-Adler reaction, that it has a double bond substituted by groups withdrawing an electron from said double bond by inductive or mesomeric effect.

Groups withdrawing an electron from said double bond by the inductive or mesomeric effect include carboxylic, anhydrous ester, cyano, nitro and sulfonate groups.

The Diels-Alder reaction is a chemical reaction used in organic chemistry, in which an alkene (dienophile) is added to a conjugated diene to form a cyclohexene derivative. In the Diels-Alder reaction, the 4 π electrons of the diene react with the alkene double bond containing 2 π electrons. For this reason, this reaction is called cycloaddition. The Adler rule allows specifying the conditions that facilitate conducting these cycloadditions: the reaction is done more easily between a diene rich in electrons and a dienophile poor in electrons. In other words, a good diene is substituted by atoms or groups of atoms that are electron donors, and a good dienophile by atoms or groups of atoms that are electron acceptors.

When said groups take electrons from said double bond by the inductive or mesomeric effect also have the possibility of being transformed into water-soluble salts by the effect of water under basic conditions, the dienophile will be called hydrolyzable dienophile.

Hydrolyzable dienophiles include maleic acid, acrylic acid, methacrylic acid and their hydrolyzable derivatives such as their esters or anhydrides.

Esters include methyl, ethyl, n-propyl or n-butyl acrylates or methacrylates, maleate esters such as dimethyl maleate or diethyl maleate.

Anhydrides include maleic anhydride and position 2 and 3 substituted derivatives thereof.

Another advantage of this novel process is that the isomeric ratio obtained from the reaction of enol phosphate with the hydrolyzable dienophile is conserved when a final step is implemented. The consequence of this is that the (E,Z) 7,9-dodecadienyl acetate synthesis process according to the present invention is much more productive than the previously-described methods, notably the process described in WO2016001383. Indeed, in the preceding invention, enol phosphate contained 20 to 25% undesirable (E,E) isomer which wastefully consumed a part of the Grignard reagent. In the present invention, the second step is therefore 20 to 25% more productive.

Description of the Process:

The first object of the present invention is a preparation process for a mixture M1 of enol phosphate isomers of formula 1.

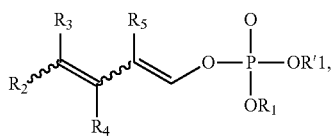

wherein $R_1$ and $R'_1$ independently designate an alkyl group or an aryl group.
$R_2$ is a linear alkyl group containing 1 to 8 carbon atoms
$R_3$, $R_4$ and $R_5$ are chosen independently from among H and $CH_3$,
free of (E,E) isomer and comprising at least 98% of (E,Z) isomer, at least 0.1% of (Z,Z) isomer and at least 0.1% of (Z,E) isomer, comprising the steps of:
  a) Contacting a mixture of enol phosphate isomers of formula 1 comprising a detectable quantity of (E,E) isomer with a hydrolyzable dienophile D, preferably in an organic solvent S, at a temperature T, and
  b) Basic hydrolysis of the medium obtained and elimination of the adduct formed.

In one particular embodiment, $R_1$ and $R_2$ independently designate an alkyl group chosen from C1-C6 alkyls, linear or branched, and an aryl group chosen from among phenyl, benzyl, mesityl or tolyl. The linear or branched C1-C6 alkyl group may be chosen from methyl, ethyl, propyl, isopropyl, butyl, n-butyl, sec-butyl, isobutyl, tert-butyl, pentyl or hexyl.

The enol phosphate isomer mixture comprising a detectable quantity of (E,E) isomer may particularly be obtained from (E) hex-2-enal as described in application WO2016001383.

In the present invention, the expression "detectable quantity" means a quantity greater than 0.10%, or even greater than 0.2% by weight, which constitutes the regulatory pharmacopeia standard to consider an impurity as negligible or not. As a corollary, a non-detectable quantity corresponds to a quantity less than 0.2%, or even less than 0.1% by weight.

The invention also relates to a process to obtain a mixture M2 of isomers of a compound of formula 3.

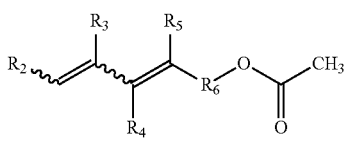

wherein $R_2$ is a linear alkyl group comprising 1 to 8 carbon atoms, $R_3$, $R_4$ and $R_5$ are independently chosen from among H and $CH_3$, $R_6$ represents a linear or branched $C_1$-$C_6$ alkyl group, characterized in that its isomeric purity is greater than or equal to 98% in (E,Z) isomer and in that it contains at least 0.1% of (Z,E) and (Z,Z) isomers and less than 1% of (E,E) isomer, comprising the steps according to claim 1 or 2, and moreover comprising a step c) of contacting mixture M1 of enol phosphate isomers of formula 1 free of (E,E) isomer and comprising at least 98% of (E,Z) isomer, at least 0.1% of (Z,Z) isomer and at least 0.1% of (Z,E) isomer obtained at step b) with a compound of formula XMg—$R_6$—OMgX, wherein each X independently represents a halogen atom, and $R_6$ represents a linear or branched $C_1$-$C_6$ alkyl group, then contacting the mixture obtained with an acylation agent.

The process according to the invention may also comprise a step c) of contacting mixture M1 of enol phosphate monomers of formula 1 free of (E,E) isomer and comprising at least 98% of (E,Z) isomer, at least 0.1% of (Z,Z) isomer and at least 0.1% of (Z,E) isomer obtained at step b) with a compound of formula XMg—$R_6$—OMgX, wherein each X independently represents a halogen atom, preferably Br or Cl, in particular Cl, and $R_6$ represents any group whatever, preferably a linear or branched C1-C6 alkyl group, more preferably a linear C1-C6 alkyl group, in particular a hexyl group, then contacting the mixture obtained with an acylation agent. This step c) produces a mixture M2 of isomers of a compound of formula 3 comprising at least 98% of (E,Z), isomer, at least 0.1% of (Z,Z) isomer and at least 0.1% of (Z,E) isomer.

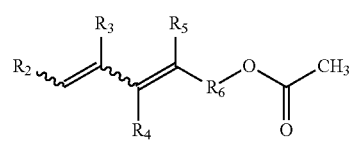

$R_2$, $R_3$, $R_4$, $R_5$ and $R_6$ have the meanings as explained further on.

Preferably, the compound of formula 1 is a compound of formula 2.

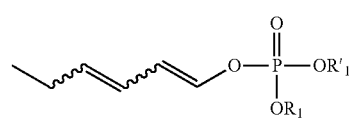

wherein $R_1$ and $R'_1$ independently designate an alkyl group or an aryl group. This alkyl group may be chosen from among C1-C6 linear or branched alkyls, and this aryl group may be chosen from among phenyl, benzyl, mesityl or tolyl. This linear or branched C1-C6 alkyl group may be chosen from methyl, ethyl, propyl, isopropyl, butyl, n-butyl, sec-butyl, isobutyl, tert-butyl, pentyl or hexyl.

Preferably, temperature T is greater than or equal to 60° C., preferably greater than or equal to 70° C., in particular equal to 70° C.

Preferably, the hydrolyzable dienophile D is chosen from among maleic acid, acrylic acid, methacrylic acid or their hydrolysable derivatives such as their esters or anhydrides. In particular, it is maleic anhydride. Preferably, the hydrolysable dienophile D is hydrophilic.

The number N of hydrolyzable dienophile D equivalents added in step a) of the process according to the invention can be any quantity appropriate for the reaction to occur with the best yield. Preferably, N is comprised between 0.25 and 10, particularly between 0.5 and 2.

Preferably, the organic solvent S is an organic solvent having a boiling point greater than 70° C. at atmospheric pressure, such as alkanes, aromatics or polar solvents. Preferably, S is methylcyclohexane.

Step b) may be implemented by addition, to the solution obtained from step a), preferably after cooling, of a basic aqueous solution and recovery of the organic products by extraction with an apolar solvent such as an alkane, an aromatic solvent or a mixture thereof.

Preferably, the acylation agent is chosen in the group made up of acetoyl halides, acetic anhydride and alkyl acetates such as ethyl acetate.

Acetylation is a reaction that introduces a functional acetyl group into an organic compound. This is a particular case of acylation. It is thus the process for introducing an acetyl (—CO—CH3) into a compound, to be precise by substitution of an active hydrogen atom by an acetyl group. Acetylation of the hydrogen of a hydroxyl group thus forms an acetoxy group: —O—CO—CH3 which is therefore an ester acetate.

In one particular embodiment, the process of the invention comprises, in a first step, obtaining a enol phosphate compound of formula 1 in the form of a mixture of isomers conforming to the protocol described in WO2016001383 and diagramed below in the case of an enol phosphate of formula 2.

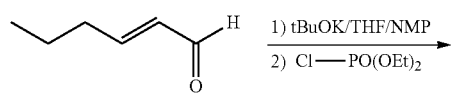

The mixture obtained is then washed with water at pH>8 to eliminate salts, excess chlorophosphate and NMP (N-methylpyrrolidone).

Then an organic solvent S is added, with a boiling point greater than 70° C., such as alkanes, aromatics, or polar solvents. These solvents include heptane, methylcyclohexane, mineral oils, toluene, xylene, dimethylbenzene, methyl THF, dimethyl formamide and dimethyl sulfoxide. Then a number N of equivalents is added, (N comprised between 0.25 and 10, particularly between 0.5 and 2) of a hydrolyzable dienophile D such as maleic acid, acrylic acid, methacrylic acid or their hydrolyzable derivatives such as esters or anhydrides, more particularly maleic anhydride. Preferably, the hydrolysable dienophile D is maleic anhydride. The mixture is then heated to a temperature T greater than or equal to 60° C. until (E,E) isomer disappears. The reaction is monitored by chromatographic techniques known to the skilled person. The reaction time depends on the number of dienophile equivalents, its nature and the temperature chosen for the reaction. After cooling, a basic solution is added and the organic products are recovered by extraction with an apolar solvent such as an alkane or an aromatic solvent. This purification is diagramed in the diagram below in the case of an enol phosphate of formula 2.

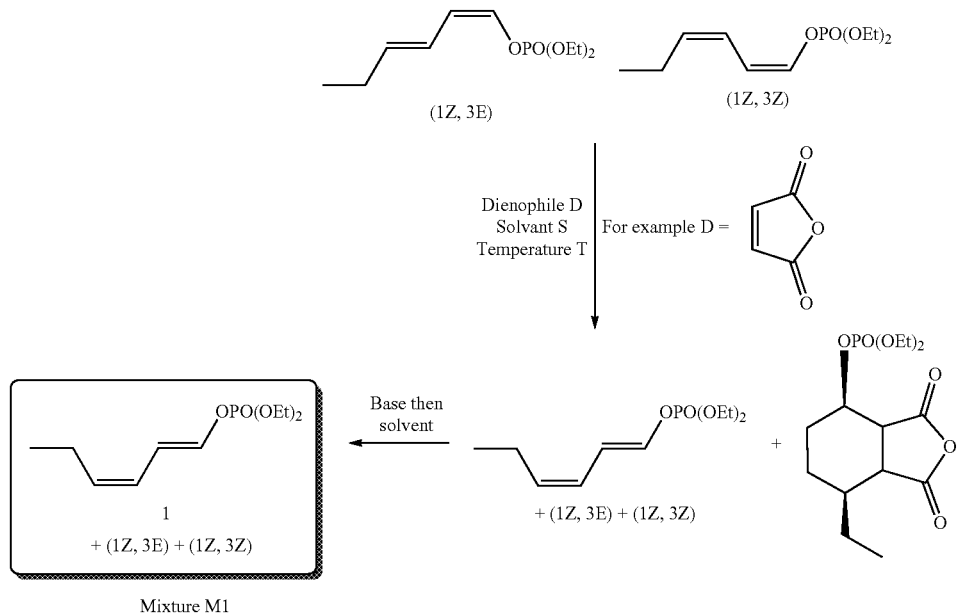

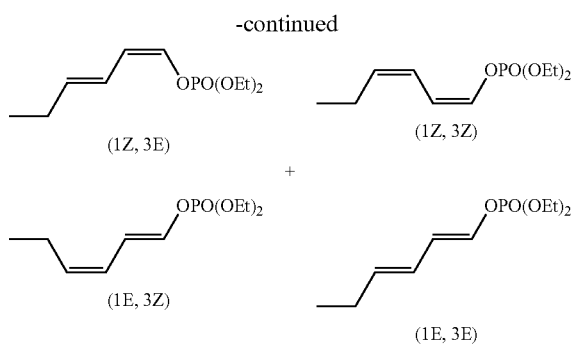

The fractions extracted are assembled and concentrated under partial vacuum. Then a mixture M1 of (E,Z), (Z,E), and (Z,Z) isomers of enol phosphate 1 characterized in that its isomeric purity is greater than or equal to 98% in (E,Z) isomer and that M1 contains at least 0.1% of (Z,E) isomer and at least 0.1% (Z,Z) isomer. This mixture M1 of diethylhexa-1,3-dien-1-yl phosphate isomers is another subject of the present invention.

A second subject of the present invention is therefore a mixture M1 of enol phosphate isomers of formula 1 free of (E,E) isomer and comprising at least 98% of (E,Z) isomer, at least 0.1% of (Z,Z) isomer and at least 0.1% of (Z,E) isomer.

Mixture "free of (E,E) isomer" means a mixture in which the (E,E) isomer cannot be detected by standard analysis techniques known to the skilled person that allow differentiating the different isomers. For example, the analysis techniques may be nuclear magnetic resonance (NMR) or gas chromatography (GC), preferably GC.

Generally, in the present invention, the proportions of different isomers and isomeric purities can be determined by the skilled person by any suitable quantitative technique, notably by NMR, high-performance liquid chromatography (HPLC) or GC, in particular by GC.

The process according to the invention may then comprise a step consisting of transforming this isomer mixture according step 2 of the protocol described in WO2016001383 to obtain an isomer mixture M2 of a compound of formula 3, in particular 7,9-dodecadienyl-1-acetate, characterized in that its isomeric purity is greater than or equal to 98% in (E,Z) isomer and that M2 contains at least 0.1% of (Z,E) and (Z,Z) isomers and less than 1% of (E,E) isomer by simple evaporation of the volatile compounds. Mixture M2 is another subject of the present invention.

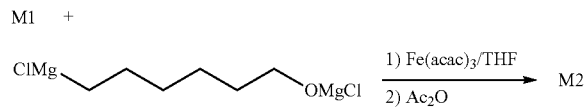

A third subject of the present invention is a mixture M2 of isomers of a compound of formula 3, wherein $R_2$ is such as described below, comprising at least 98% of (E,Z) isomer, at least 0.1% of (Z,Z) isomer and at least 0.1% of (Z,E) isomer.

Providing a process for obtaining mixture M2 is also an object of the present invention, comprising contacting mixture M1 of enol phosphate monomers of formula 1 free of (E,E) isomer and comprising at least 98% of (E,Z) isomer, at least 0.1% of (Z,Z) isomer and at least 0.1% of (Z,E) with a compound of formula $XMg-R_6-OMgX$, in which each X independently represents a halogen atom, preferably Br or Cl, in particular Cl, and $R_6$ represents a linear or branched C1-C6 alkyl group, preferably a linear C1-C6 alkyl group, in particular hexyl, then contacting the mixture obtained with an acylation agent.

Preferably, the acylation agent is chosen in the group made up of acetoyl halides, acetic anhydride and alkyl acetates such as ethyl acetate.

EXAMPLES

The raw materials and solvents are raw materials available commercially from Sigma Aldrich.

The enol phosphate (diethyl-hexa-1,3-dienyl phosphate) is synthesized by applying the process described in WO2016001383.

The Grignard reagent is prepared from 6-chloro-hexan-1-ol, n-butyl magnesium chloride and magnesium.

The analytical method consists of gas chromatography (GC) analysis on a HP 5890 Series II device equipped with a FID detector. The chromatographic column is a Innowax 30 m, 0.25 mm, 0.25 µm column, the carrier gas is helium and the pressure is 11 psi.

The furnace follows the following temperature profile: T0=150° C., Initial time 10 min.

Gradient 20°/min; Final temperature: 200° C. Duration 7 min.

The injector is at 250° C., the detector at 300° C.

The volume injected is 1 µl. The concentration of the sample is 4 g/L in ethyl acetate (ETAC).

The reactions are conducted in a 20-L reactor with mechanical stirring (400 rpm), equipped with a thermometer and a nitrogen inlet. The system is cooled with a cryostat as necessary.

Example 1 (Non-Invention): Improvement of the Isomeric Purity of a Mixture of 7,9-Dodecadienyl Acetate Isomers by Treatment with Urea A 20-L glass reactor is loaded with 2.94 kg (8.92 equiv.) of urea and 11.8 L (5.9 vol) of methanol then stirring is started while maintaining the temperature at 55±5° C. until complete dissolution of the solids.

2065 g (1 equiv.) of a mixture of 7,9-dodecandienyl acetate isomers is added so that the internal temperature of the reactor does not go below 40° C. The temperature is maintained at 40±5° C. for one hour, then lowered to 20±5° C. in 3 hours. Crystallization starts during this cooling. The reaction mixture is then stirred at 20±5° C. for more than 12 h, then the temperature is lowered by 5° C. per hour until a temperature of 5° C. is obtained that is maintained for 2.5 h while continuing to stir. The solids are then removed by vacuum filtration of the reaction mixture. The products are then washed with methanol (500 ml) and concentrated by vacuum filtration, then washed with stirring with a mixture of water (2 vol) and MTBE (1.15 vol). After phase separation, the aqueous phase is removed and the organic phase is concentrated. 1334 g of a new mixture of 7,9-dodecadienyl acetate isomers is obtained, or a yield of 65%.

After this first inclusion in urea of 2065 g of a mixture of pheromone isomers, which leads to 1334 g of enriched pheromone, a second inclusion in urea is done in a 1-L reactor, with 100 g of the enriched batch (same protocol as the one described previously while keeping the proportionality of reaction agents). A third inclusion is then conducted with 62.6 g of doubly enriched pheromone isomer mixture still with the same protocol.

The isomeric purity of the products after one, two or three inclusions of urea is characterized by gas chromatography and the result presented in the table below is obtained.

|  | Isomer (7Z, 9Z) | Isomer (7Z, 9Z) | Isomer (7Z, 9Z) | Isomer (7Z, 9Z) |
| --- | --- | --- | --- | --- |
| Initial mixture of 7,9-dodecadienyl acetate isomers | 0.86% | 80.23% | 1.13% | 17.78% |
| after first purification with urea | 1.33% | 91.85% | 1.35% | 5.47% |
| after second purification with urea | 1.88% | 92.78% | 0.66% | 4.68% |
| after third purification with urea | 2.75% | 91.57% | 0.35% | 5.33% |

It is observed that such a treatment with urea is time-consuming and tedious and does not allow reaching very high purities, even by doing several successive purifications with urea Thus, after three successive treatments with urea following the protocol described previously, a ceiling is attained with around 5% of (E,E) isomer, furthermore, a part of the pheromone is degraded.

Example 2 (Non-Invention): Improvement of the Isomeric Purity of a Mixture of 7,9-Dodecadienyl Acetate Isomers by Direct Action of a Hydrolyzable Dienophile Into a 250-mL four-necked flask are introduced 10 g of a mixture of 7,9-dodecandienyl acetate isomers (44.6 mmol) (isomeric purity given in the table below), 40 ml of methylcyclohexane and 4.37 g of maleic anhydride (hydrolyzable dienophile D) (44.6 mmol; 1.0 equiv.).

The reaction mixture is heated at T=70° C. for 3 hours and then cooled to 30° C., and a saturated $NaHCO_3$ is added (1.14 M, 50 ml).

After 30 minutes with stirring, the aqueous phase is extracted with heptane (2×20 ml), washed with a saturated aqueous solution of NaCl (5.92 M, 20 ml) and then with water (20 mL), and concentrated under vacuum.

7.5 g of the purified pheromone mixture are obtained of isomeric composition:

| Isomers | Isomeric purity in % | | | |
| --- | --- | --- | --- | --- |
| | (7Z, 9Z) | (7E, 9Z) | (7Z, 9E) | (7E, 9E) |
| 7,9-dodecadienyl acetate before treatment | 5.59 | 67.47 | 2.82 | 24.10 |
| 7,9-dodecadienyl acetate after treatment | 7.78 | 85.60 | 1.86 | 4.76 |

This non-invention example illustrates two facts:
1) The Diels-Alder reaction does not lead to a total elimination of (E,E) isomer.
2) The mass yield of this step is 75%, which means that the previous costly step (coupling reaction of enol phosphate with the magnesium compound) has its real productivity reduced by 25%.

Example 3: Improvement of the Isomeric Purity of a Mixture of Diethyl-Hexa-1,3-Bien-1-Yl Phosphate Isomers by the Process According to the Invention Leading to Mixture M1

A mixture of diethyl-hexa-1,3-dienyl phosphate isomers is obtained from trans-hexen-1-al by following the process described in patent WO2016001383.

Into the 20-L reactor are introduced 2085 g of this crude mixture of diethyl-hexa-1,3-dienyl phosphate (8.90 mol) (isomeric purity given in the table below), 8.34 L of methylcyclohexane and 523.0 g of maleic anhydride (5.33 mol, or 0.6 equiv.).

The reaction mixture is heated at T=70° C. for 3 hours and then cooled to 10° C., and an aqueous sodium hydroxide solution is added (3 M, 4.17 L).

After 30 minutes with stirring, the aqueous phase is extracted with heptane (2×3.13 L), washed with a saturated aqueous solution of NaCl (10% w/w; 1×2.09 L) and concentrated under vacuum.

1566 g of mixture M1 of diethyl-hexa-1.3-dienyl phosphate are obtained of isomeric composition:

| Isomers | Isomeric purity in % | | | |
| --- | --- | --- | --- | --- |
| | (1Z, 3E) | (1Z, 3Z) | (1E, 3Z) | (1E, 3E) |
| mixture before treatment | 1.03 | 1.07 | 73.60 | 24.30 |
| mixture after treatment M1 | 0.74 | 0.81 | 98.45 | 0 |

Example 4: Obtaining Pheromone Mixture M2 from a Purified Mixture of Diethyl-Hexa-1,3-Dien-1-Yl Phosphate Isomers From the enol phosphate mixture M1 of Example 3, the process described in WO2016001383A1 is applied to obtain pheromone mixture M2.

The following are introduced into the four-neck reactor, under nitrogen: the Grignard alcoholate reagent, prepared from 67.1 of de 6-chloro-hexan-1-ol (491.7 mmol), 474 ml of THF and magnesium (983.5 mmol).

The mixture is then cooled to 5° C. then the iron (III) acetylacetonate catalyst is added (158 mg, 0.1% mol). To this black mixture are added 97.5 g of preceding mixture M1 (416.3 mmol) in 20 minutes while keeping the temperature below 5° C.

After 2 h of stirring at 25° C., the mixture is cooled to –5° C. and 85 mL of acetic anhydride are added dropwise in 20 minutes. After one hour of stirring at room temperature, the reaction mixture is acidified by an aqueous HCl solution (1 N, 680 ml). The aqueous phase is extracted three times with methyl tert-butyl ether (3×120 ml). The three organic phases are recombined, then washed with water and concentrated under vacuum.

7,9-dodecandienyl acetate mixture M2 is then obtained (m=65.7 g). The initial overall yield of purified enol phosphate is 70% (mass purity=95%; isomeric purity=98%)

| Isomers | Isomeric purity in % | | | |
| --- | --- | --- | --- | --- |
| | (1Z, 3E) | (1Z, 3Z) | (1E, 3Z) | (1E, 3E) |
| Mixture M1 | 0.74 | 0.81 | 98.45 | 0 |
| Isomers | (7Z, 9Z) | (7E, 9Z) | (7Z, 9E) | (7E, 9E) |
| Mixture M2 | | 98.0 | | 0.9 |

The invention claimed is:
1. A process for preparing a mixture M1 of enol phosphate isomers of formula 1,

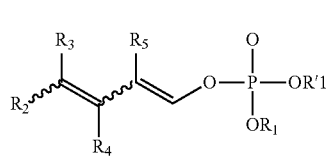

1 wherein $R_1$ and $R'_1$ are independently selected in the group consisting of an alkyl group comprising 1 to 6 carbon atoms and an aryl group, $R_2$ is a linear alkyl group comprising 1 to 8 carbon atoms, $R_3$, $R_4$ and $R_5$ are chosen independently from H and $CH_3$, free of (E,E)-isomer and comprising at least 98% of (E,Z)-isomer, at least 0.1% of (Z,Z)-isomer and at least 0.1% of (Z,E)-isomer, comprising the steps of:

a) contacting a mixture of enol phosphate isomers of formula 1 comprising a detectable quantity of (E,E)-isomer with a hydrolysable dienophile D, wherein the hydrolysable dienophile D is selected from the group consisting of maleic acid, acrylic acid, methacrylic acid, methyl acrylate, ethyl acrylate, n-propyl acrylate, n-butyl acrylate, methyl methacrylate, ethyl methacrylate, n-propyl methacrylate, n-butyl methacrylate, dimethyl maleate, diethyl maleate, and maleic anhydride, and b) basic hydrolysis of the medium obtained in step a) by addition of a basic aqueous solution and elimination of the adduct formed to obtain mixture M1, wherein the detectable quantity is a quantity above 0.1%.

2. The process according to claim 1, wherein the enol phosphate isomer mixture comprising a detectable quantity of (E,E)-isomer is obtained from (E)-hex-2-enal.

3. The process according to claim 1, wherein enol phosphate of formula 1 is a compound of formula 2,

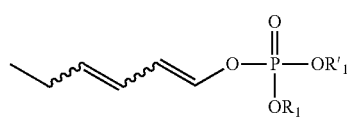

$R_1$ and $R'_1$ having the same meaning as in claim 1.

4. The process according to claim 1, wherein the hydrolysable dienophile D is maleic anhydride.

5. The process according to claim 1, wherein step a) of contacting a mixture of enol phosphate isomers of formula 1 comprising a detectable quantity of (E,E)-isomer with a hydrolysable dienophile D is performed at a temperature T, wherein temperature T is equal to 70° C.

6. The process according to claim 1, wherein step a) of contacting a mixture of enol phosphate isomers of formula 1 comprising a detectable quantity of (E,E)-isomer with a hydrolysable dienophile D is performed in an organic solvent S.

7. The process according to claim 6, wherein the organic solvent S is methylcyclohexane.

* * * * *